US008372030B2

(12) United States Patent
Dixon et al.

(10) Patent No.: US 8,372,030 B2
(45) Date of Patent: Feb. 12, 2013

(54) APPARATUS FOR AN IMPROVED HIGH PRESSURE MEDICINAL DISPENSER

(75) Inventors: Chris G. Dixon, Bloomington, IN (US); David G. Burton, Bloomington, IN (US); Scott K. Philhower, Bloomington, IN (US); Gregory A. Frankland, Unionville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1189 days.

(21) Appl. No.: 10/593,949

(22) PCT Filed: Mar. 24, 2005

(86) PCT No.: PCT/US2005/100036
§ 371 (c)(1),
(2), (4) Date: Oct. 12, 2007

(87) PCT Pub. No.: WO2005/097239
PCT Pub. Date: Oct. 20, 2005

(65) Prior Publication Data
US 2011/0125088 A1    May 26, 2011

Related U.S. Application Data

(60) Provisional application No. 60/558,040, filed on Mar. 31, 2004.

(51) Int. Cl.
*A61M 5/30* (2006.01)
(52) U.S. Cl. ........................................................ 604/68
(58) Field of Classification Search ............... 604/69–70, 604/222–223, 82, 68; 606/92
See application file for complete search history.

(56) References Cited

U.S. PATENT DOCUMENTS

| 3,212,685 | A | 10/1965 | Swan et al. |
| 4,312,343 | A | 1/1982 | Leveen et al. |
| 4,940,459 | A * | 7/1990 | Noce .......................... 604/97.02 |
| 5,927,562 | A | 7/1999 | Hammen et al. |
| 6,082,596 | A * | 7/2000 | Koch et al. ..................... 222/390 |
| 6,645,213 | B2 * | 11/2003 | Sand et al. ...................... 606/92 |
| 6,802,824 | B2 * | 10/2004 | Mickley et al. .......... 604/164.12 |
| 2002/0016603 | A1 | 2/2002 | Wells |
| 2002/0032447 | A1 | 3/2002 | Stuart et al. |
| 2004/0204715 | A1 * | 10/2004 | Evans et al. ..................... 606/92 |

FOREIGN PATENT DOCUMENTS

| EP | 0 919 206 | 6/1999 |
| WO | WO 95 22941 A | 8/1995 |
| WO | WO 01 93787 A | 12/2001 |
| WO | WO 2004/002375 A | 1/2004 |

* cited by examiner

*Primary Examiner* — Nicholas Lucchesi
*Assistant Examiner* — Melissa A Snyder
(74) *Attorney, Agent, or Firm* — Woodard, Emhardt, Moriarty, McNett & Henry LLP

(57) ABSTRACT

An apparatus for an improved high pressure medicinal dispenser is disclosed. The high pressure dispenser may include a handle (26), a chamber (18), a threaded region, a threaded rod (14), and a knob (20). The high pressure dispenser may have at least one insert-molded component. A threaded insert providing the threaded region may be insert-molded into the handle or the threaded rod may be insert-molded into the knob, or both. The dispenser may have a handle made of hard plastic and overmolded soft rubber material. The dispenser also may have a ribbed knob having at least one longitudinal rectangular cavity. Furthermore, the dispenser may have a chamber that has an interior concave surface and an interior convex surface between the interior cylindrical surface of the chamber and a nozzle. The chamber may have at least one tab or notch dimensioned to engage with at least one corresponding notch or tab on the handle.

19 Claims, 6 Drawing Sheets

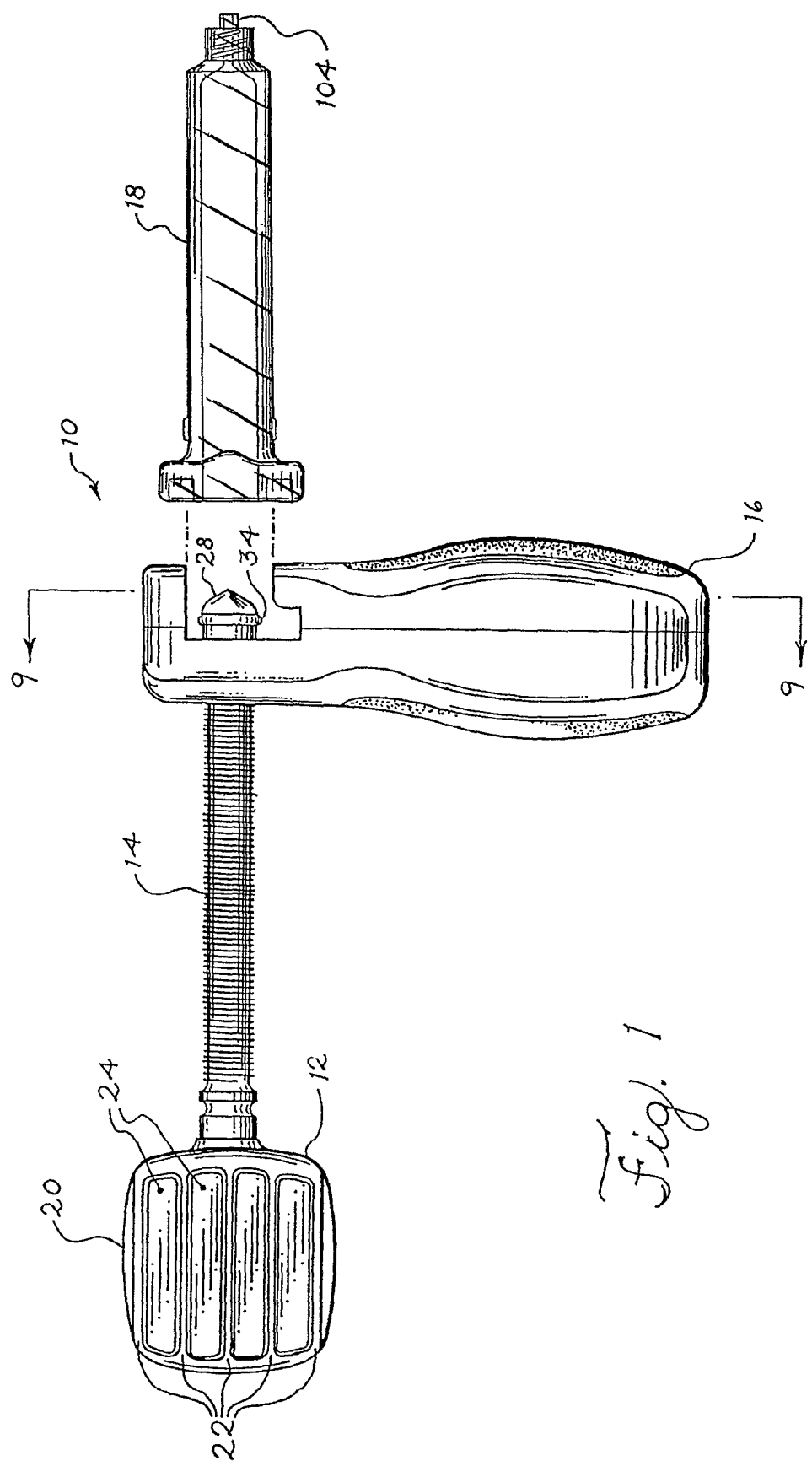

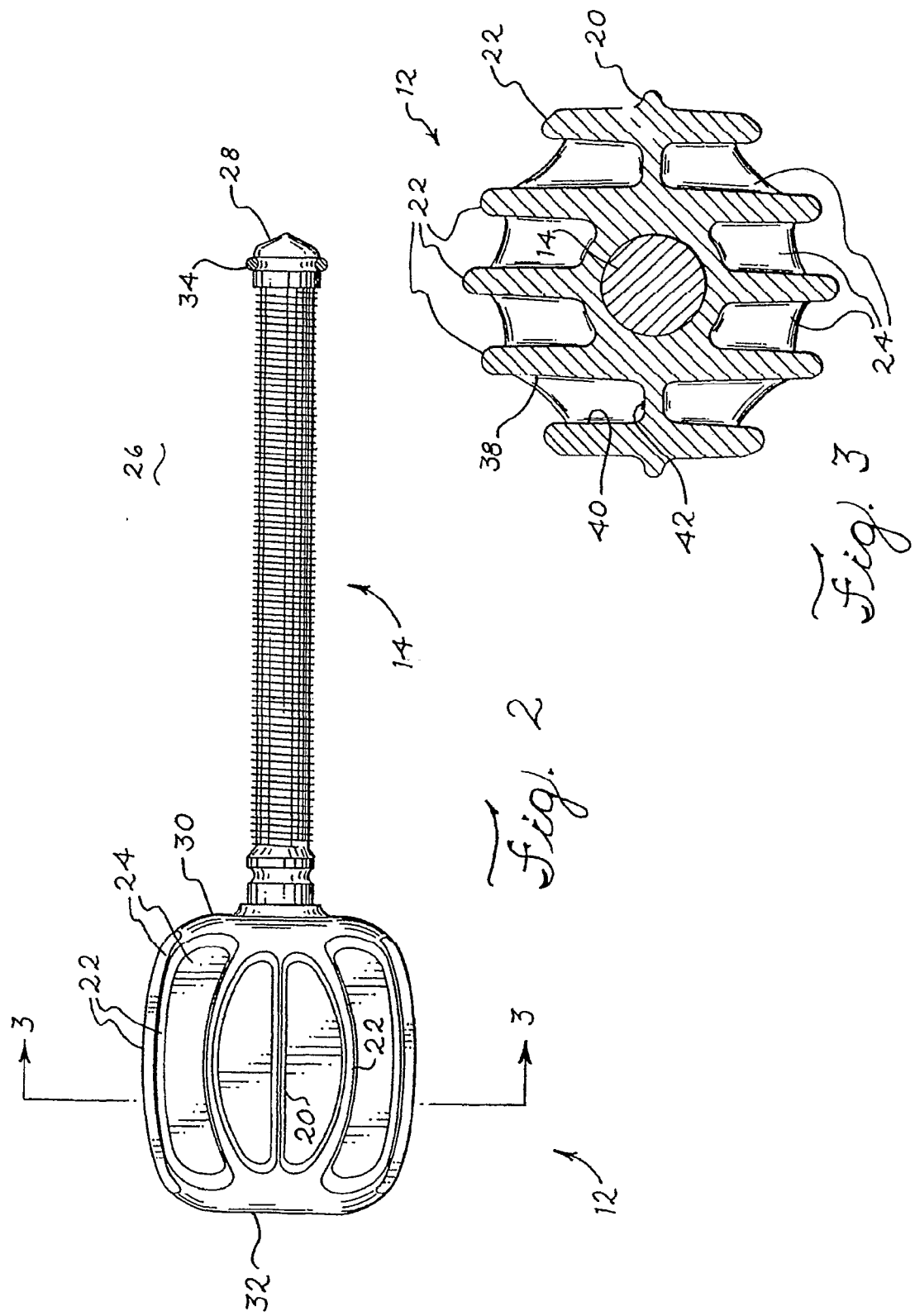

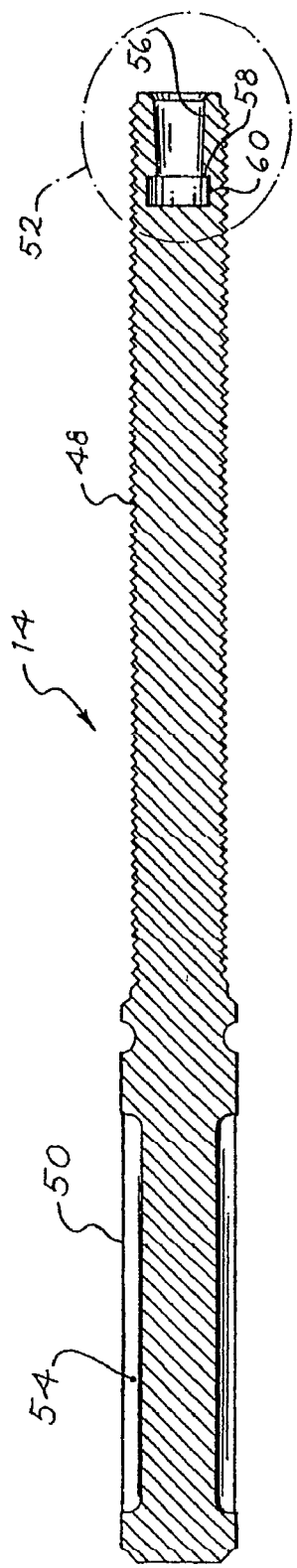
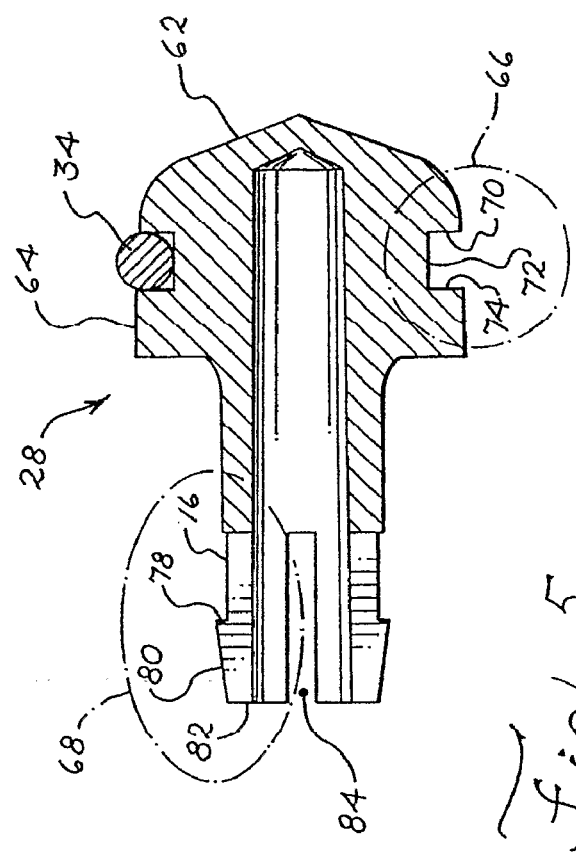
Fig. 4
Fig. 5

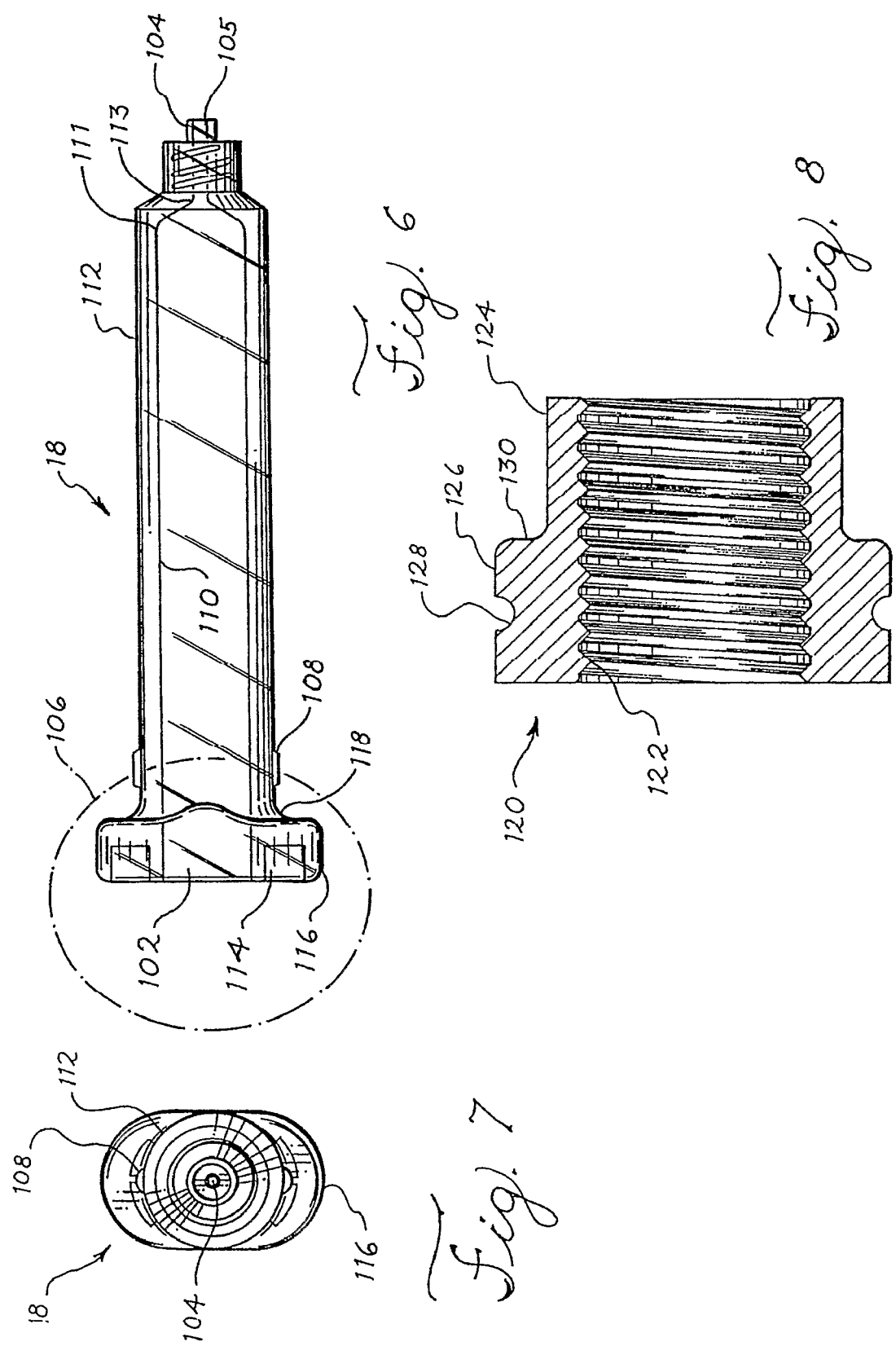

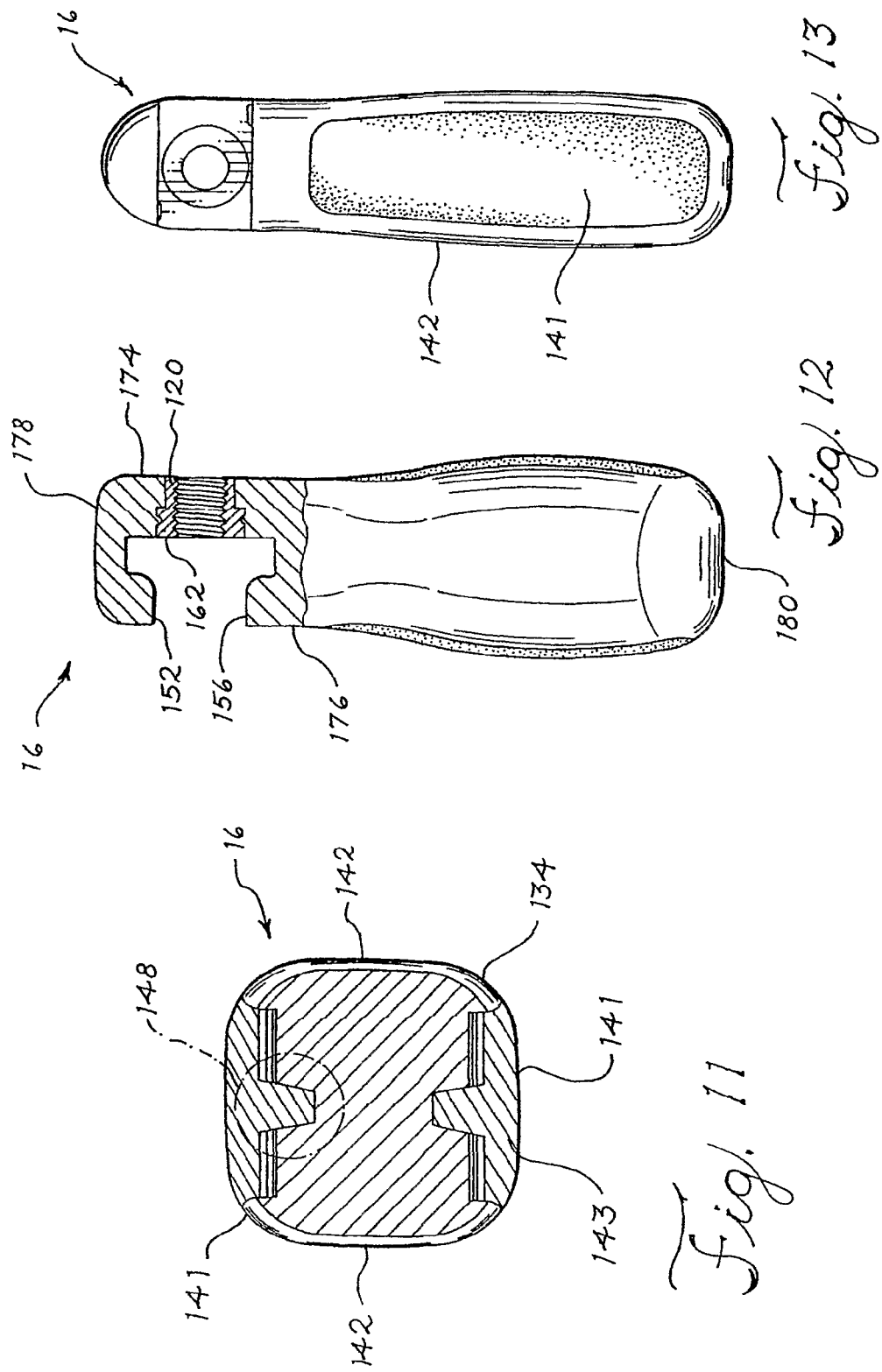

APPARATUS FOR AN IMPROVED HIGH PRESSURE MEDICINAL DISPENSER

REFERENCE TO RELATED APPLICATIONS

This application claims the benefit under 35 U.S.C. §365 of PCT/US2005/010036 filed Mar. 24, 2005 and under 35 U.S.C. §119(e) of U.S. provisional application Ser. No. 60/558,040, filed on Mar. 31, 2004, entitled "Apparatus for an Improved High Pressure Medicinal Dispenser," both of which are hereby incorporated by reference herein in their entireties.

This application claims the benefit of provisional application Ser. No. 60/558,040, filed on Mar. 31, 2004, entitled "Apparatus for an Improved High Pressure Medicinal Dispenser."

FIELD OF THE INVENTION

The present invention relates generally to high pressure medicinal dispensers. More particularly, the invention relates to an apparatus for an improved high pressure medicinal dispenser or injector having increased strength and enhanced ergonomic and flow characteristics.

BACKGROUND OF THE INVENTION

High pressure medicinal dispensers are utilized to inject either fluid or semi-fluid medicinal mixtures under high pressure to desired locations in precisely measured amounts and with only minimal manual force applied. Typically, the high pressure dispenser has a syringe barrel with a cylindrical body and a nozzle at one end, such as disclosed by U.S. Pat. No. 4,312,343. A threaded rod may be attached to a knob at one end and a piston at the other. The threaded rod and syringe barrel are commonly held together by a collar. In operation, the knob is utilized to manually rotate the threaded rod, moving the rod into the cylindrical body of the syringe barrel, which allows the piston, attached to one end of the threaded rod, to move the mixture within the cylindrical body of the syringe barrel through the nozzle and to a desired location. Additionally, some conventional designs have a handle interconnected with the syringe barrel.

However, the overall strength of the conventional devices may be limited by the manner in which the individual dispenser components are manufactured and interconnected. The limitations placed upon the strength of the overall conventional devices, as well as the individual high pressure dispenser components, limits the pressure at which the mixture can be injected and the pressure that the dispenser can physically withstand.

Moreover, conventional high pressure dispensers have poor ergonomic characteristics. For example, conventional handles are very small in diameter. Additionally, conventional knobs have relatively short axial lengths. Hence, the disadvantages exhibited by the conventional devices include limitations pertaining to the ability of an operator to maintain manual control of the high pressure dispenser, as well as manually rotate the threaded rod.

Additionally, conventional syringe barrels have sharp angles on the interior of the syringe barrel between the cylindrical interior surface of the syringe barrel and the nozzle. As a result of the sharp angles, the interior surface of the syringe barrel has a funnel or conical shaped transition from the cylindrical interior surface to the nozzle. However, such a design yields poor flow characteristics when used with viscous fluids at high pressure.

The present invention alleviates one of more of the shortcomings described above.

BRIEF SUMMARY

The present invention provides a high pressure dispenser with enhanced strength by having at least one insert-molded component. The present invention also provides an apparatus that enhances the handling and control of a high pressure dispenser, as well as the ability of a user to rotate the threaded rod at high pressure, by overcoming the limitations previously imposed by conventional designs. Additionally, the present invention provides an apparatus that improves the ergonomic and flow characteristics of a high pressure dispenser.

In one embodiment of the present invention, a high pressure dispenser may include a chamber, a threaded region, a handle, a threaded rod, a knob, and at least one insert-molded component, where the insert-molded component may either be a threaded insert insert-molded into the handle or the threaded rod insert-molded into the knob, or both.

In another embodiment of the present invention, a high pressure dispenser may include a chamber, a knob, a threaded rod, a threaded region, and a handle including overmolded soft rubber material. The handle also may include hard plastic.

In another embodiment of the present invention, a high pressure dispenser may include a chamber, a handle, a threaded region, a threaded rod, and a knob. The chamber may have an exterior surface having at least one tab or notch dimensioned to engage with at least one corresponding notch or tab on an exterior surface of the handle.

In yet another embodiment of the present invention, a high pressure dispenser may include a chamber, a knob, a threaded region, a threaded rod, and a handle. The chamber may have an interior cylindrical surface in fluid communication with a nozzle via an interior smooth concave surface.

Advantages of the present invention will become more apparent to those skilled in the art from the following description of the preferred embodiments of the invention which have been shown and described by way of illustration. As will be realized, the invention is capable of other and different embodiments, and its details are capable of modification in various respects. Accordingly, the drawings and description are to be regarded as illustrative in nature and not as restrictive.

BRIEF DESCRIPTION OF THE DRAWINGS

FIG. 1 is a longitudinal view of one embodiment of the high pressure dispenser of the present invention;

FIG. 2 is a side elevation view of one embodiment of the knob and threaded rod of the present invention;

FIG. 3 is a cross-sectional view of one embodiment of the knob of the present invention;

FIG. 4 is a longitudinal cross-sectional view of one embodiment of the threaded rod of the present invention;

FIG. 5 is a longitudinal cross-sectional view of one embodiment of the piston of the present invention;

FIG. 6 is longitudinal view of one embodiment of the chamber of the present invention;

FIG. 7 is a front elevation view of one embodiment of the chamber of the present invention;

FIG. 8 is longitudinal cross-sectional view of one embodiment of the threaded insert of the present invention;

FIG. 11 is a cross-sectional view of one embodiment of the handle of the present invention;

FIG. 12 is a cross-sectional view of one embodiment of the handle of the present invention; and FIG. 13 is a longitudinal view of one embodiment of the handle of the present invention.

DETAILED DESCRIPTION

Figures 9, 10:
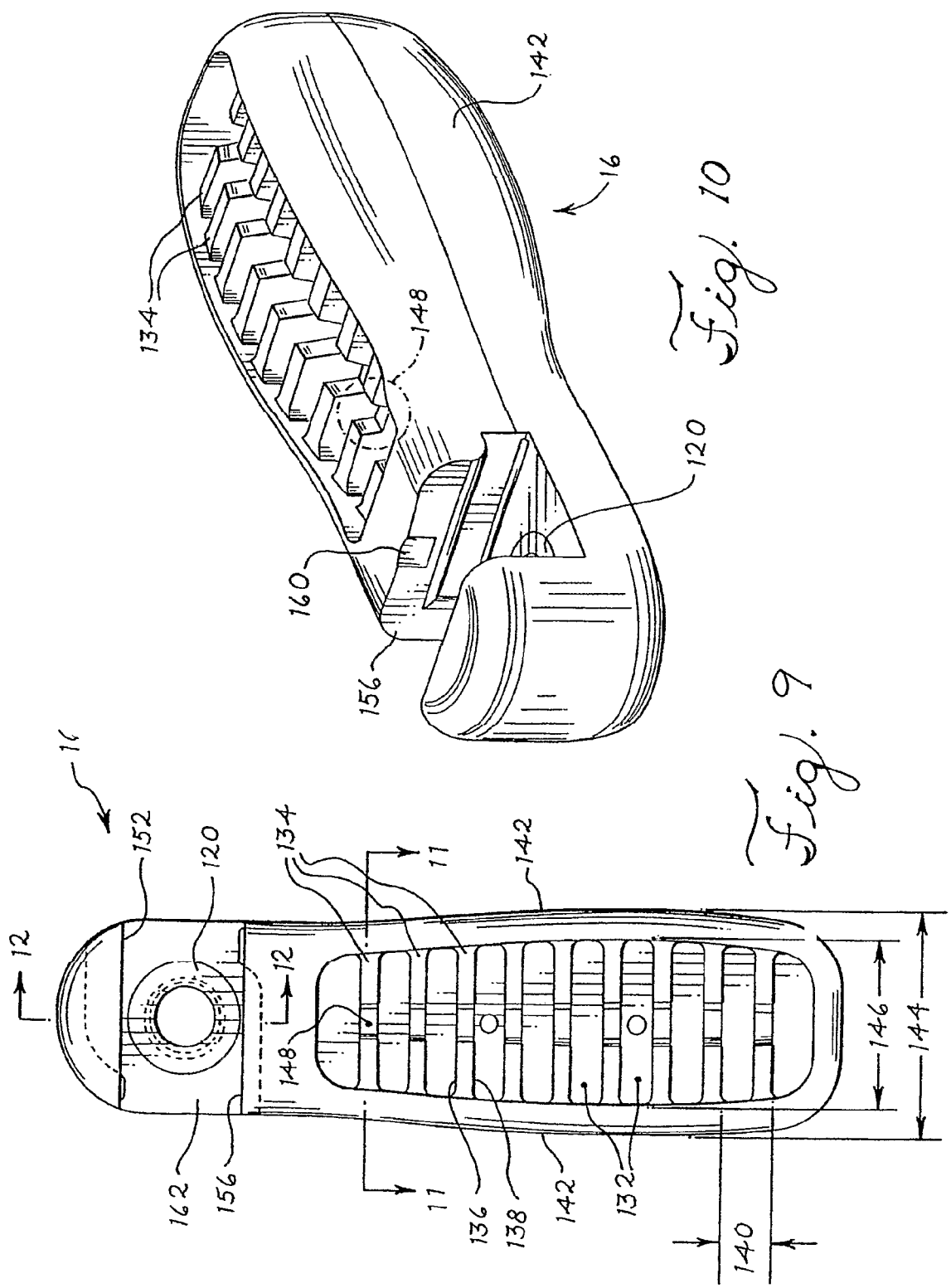
FIG. 9 is a cross-sectional view of one embodiment of the handle of the present invention.
FIG. 10 is a perspective view of one embodiment of the handle of the present invention.

In accordance with the present invention, an apparatus is provided that may enhance the overall strength of a high pressure medicinal dispenser. In the embodiments provided, a high pressure medicinal dispenser is disclosed which may have at least one insert-molded component. The insert-molded component may include either the threaded rod insert-molded into the knob or the threaded insert insert-molded into the handle, or both.

The high pressure dispenser provided also may enhance the ergonomic characteristics of the high pressure dispenser. The apparatus provided may improve the ability of a user to handle and control a high pressure medicinal dispenser, as well as rotate the threaded rod with respect to the handle. The high pressure dispenser may have a handle that includes over-molded soft rubber material. Additionally, the high pressure dispenser may have a knob having at least one longitudinal cavity or an axial length approximately equal to or greater than the diameter of the knob.

In yet another embodiment, the apparatus provided may improve the flow characteristics for viscous fluids at high pressure. The high pressure dispenser may have a chamber with an interior longitudinal concave surface between the cylindrical interior of the chamber and the nozzle.

FIG. 1 illustrates a longitudinal view of a high pressure medicinal dispenser 10. The high pressure dispenser 10 may be utilized to inject medicinal mixtures, whether fluid or semi-fluid, to the desired locations. The high pressure dispenser 10 may have a knob 12, a threaded rod 14, a handle 16, a chamber 18, and a threaded region or insert (not shown). The high pressure dispenser 10 may have other configurations including those with fewer or additional components.

The threaded rod 14 may be insert-molded into the center of the knob 12. The threaded rod 14 may be fabricated from metal and the knob 12 may be fabricated from plastic. In another embodiment, the threaded rod 14 may be an extension of the knob 12 (not shown). For example, if the knob 12 and the threaded rod 14 are plastic; the threaded rod 14 may be fabricated by forming the knob and threading a portion of a single plastic casting or machined from a single piece of metal, such as stainless steel. In the same way, the threaded region may be integral to the handle 16. The knob 12 and the threaded rod 14 also may be fabricated from multiple pieces of plastic.

The overall strength of the high pressure dispenser 10 may be increased by insert-molding the threaded rod 14 into the knob 12. The increase in the overall strength of the high pressure dispenser 10 may permit the pressure at which the dispenser 10 may inject medicinal mixtures, as well as the pressure that the dispenser 10 may physically withstand without mechanical failure or leakage, to increase.

The threaded rod 14 may be coupled to the handle 16. The threads of the threaded rod 14 may engage a threaded region within the handle 16. The threaded region may have internal threads. The internal threads may be integral to the handle 16 or may be provided by a threaded insert 120, as will be discussed with regard to FIG. 8. In use, the knob 12 may be used to turn the threaded rod 14 in either a clock-wise or counter clock-wise direction.

The threaded rod 14 also may be coupled to a piston 28. The piston 23 may have an o-ring 34. The o-ring 34 may be sized to engage the interior surface of the chamber 18, which may hold a medicinal mixture. The chamber 18 may be coupled to the handle 16 at one end and may have a nozzle 104, through which the medicinal mixture may be dispensed, at the other end.

After the components are assembled into the high pressure dispenser 10, a user may hold the handle 16 with one hand and turn the knob 12 with the other. Turning the knob 12 in a clock-wise direction may move the threaded rod 14 further into the chamber 18. Turning the knob 12 in a counter clock-wise direction may move the threaded rod 14 further out of the chamber 18. The o-ring 34 of the piston 28 may achieve a fluid tight engagement with the interior of the chamber 18, ensuring that the medicinal mixture will be injected via the nozzle 104 as the piston 28 is advanced toward the nozzle 104. The high pressure dispenser 10 may inject medicinal mixtures at pressures of 2000 psi (13.8 MPa) and higher. In one embodiment, the dispenser 10 also may inject medicinal mixtures at pressures of about 3500 psi (24.1 MPa).

The knob 12 may have a symmetrical rib 20 and a number of longitudinal ribs 22. The symmetrical rib 20 and the longitudinal ribs 22 may each be in a plane parallel to the longitudinal axis of the threaded rod 14. The exterior surface of the symmetrical rib 20 and the longitudinal ribs 22 may be curved outward or convex.

The body of the knob 12 may have at least one longitudinal cavity 24. Each longitudinal cavity 24 may be an indentation into the body of the knob 12 and may be between a pair of corresponding longitudinal ribs 22. Each longitudinal cavity 24 may be parallel to the longitudinal axis of the threaded rod 14.

FIG. 2 is a side elevation cross-sectional view of a plunger 26. The plunger 26 may include the knob 12, the threaded rod 14, and a piston 28. The plunger 26 may have other configurations including those with fewer or additional components.

The unique features of the knob 12, such as the longitudinal ribs 22, the longitudinal cavities 24, and the longitudinal length of the knob 12 being approximately equal to or greater than diameter of the knob 12, may enhance the capability of the user to operate and control the high pressure dispenser 10, as well as the ergonomic characteristics of the dispenser 10. The unique features of the knob 12 also may allow a user to exert more torque upon the plunger 26.

The knob 12 may be coupled to the threaded rod 14. The knob 12 may have a distal surface 30 and a proximal surface 32. The distal and proximal surfaces 30, 32 both may be smooth and substantially orthogonal to the longitudinal axis of the knob 12.

The axial length of the knob 12 may be approximately equal to or greater than the diameter of the knob 12 that is orthogonal to the longitudinal axis of the threaded rod 14. For example, the axial length of the knob 12 from the distal surface 30 to the proximal surface 32 may be approximately 51 mm or greater. In another embodiment, the diameter of the knob 12 may culminate at approximately 51 mm.

Each longitudinal cavity 24 may extend the majority of the axial length of the knob 12 and may be an indentation with four inwardly protruding walls. The four inwardly protruding walls may include the distal surface 30, the proximal surface 32, and a pair of longitudinal ribs 22. Each longitudinal cavity 24 may be substantially perpendicular to the symmetrical rib 20.

The threaded rod 14 may be coupled at its distal end to the piston 28. The piston 28 may have a gland or seating mechanism for an o-ring 34. The surface of the piston 28 under the o-ring 34 may have a number of longitudinal grooves which provide for air aspiration during use.

FIG. 3 is a cross-sectional view of the knob 12 along line 3-3 of FIG. 2, perpendicular to the longitudinal axis of the medicinal dispenser. The knob 12 may have a symmetrical rib 20, longitudinal ribs 22, and longitudinal cavities 24. The knob 12 may have other configurations including those with fewer or additional components.

The knob 12 may have a solid interior that surrounds the threaded rod 14. The proximal end of the threaded rod 14 may be insert-molded into the center of the knob 12.

The two halves of the knob 12 on either side of the symmetrical rib 20 may be identical. The symmetrical rib 20 may intersect the longitudinal axis of the threaded rod 14.

The longitudinal ribs 22 may be substantially perpendicular to the symmetrical rib 20. The longitudinal ribs 22 may be approximately parallel with respect to each other. In one embodiment, the distance from one longitudinal rib 22 to the next may be approximately 10 mm.

Each longitudinal cavity 24 may have a right surface 38, a left surface 40, and a bottom surface 42. The juxtaposition of each right surface 38, left surface 40, and bottom surface 42 of each longitudinal cavity 24 may form a u-shaped protuberance into the cross-sectional exterior of the knob 12. In one embodiment, the knob 14 may have eight longitudinal cavities 24.

FIG. 4 is an enlarged longitudinal cross-sectional view of the threaded rod 14. The threaded rod 14 may have a threaded portion 48, a knurled portion 50 and an internal locking mechanism 52. The threaded rod 14 may have other configurations including those with fewer or additional components. In one embodiment, the threaded rod 14 may have a longitudinal length of approximately 161 mm.

The threaded portion 48 may have a number of uniform threads. In one embodiment, the threaded portion 48 may have a longitudinal length of approximately 101 mm.

The knurled portion 50 may have an exterior surface generally cylindrical in shape. The knurled portion 50 may have at least one knurl 54. Each knurl 54 may be a longitudinal notch or an indentation into the interior of the threaded rod 14. Each knurl 54 may be primarily rectangular in shape and extend the majority of the knurled portion 50. When the threaded rod 14 is insert-molded into the knob 12 (FIG. 1), each knurl 54 may help assist in coupling the threaded rod 14 to the knob 12 such that the threaded rod 14 rotates as the knob 12 is turned by a user. In one embodiment, the knurled portion 50 may have a longitudinal length of approximately 59 mm and may have an outer diameter of approximately 13 mm.

The internal locking mechanism 52 may have an internal tapered surface 56, an internal annular surface 58, and an internal tubular surface 60. In one embodiment, the internal locking mechanism 52 may have a longitudinal length of approximately 13 mm.

The internal tapered surface 56 may be generally smooth and conical in shape. In one embodiment, the longitudinal length of the internal tapered surface 56 may be approximately 10 mm. In another embodiment, the internal tapered surface 56 may have a cross-section orthogonal to the threaded rod 14 that may be approximately 7 mm at the distal end of the threaded rod 14.

The internal annular surface 58 may intersect the internal tapered surface 56 at an angle less than 90 degrees. In one embodiment, the inner diameter of the internal annular surface 58 may be approximately 6 mm.

The internal tubular surface 60 may be substantially parallel to the longitudinal axis of the threaded rod 14. The internal tubular surface 60 may intersect the interior annular surface 58 at an angle of approximately 90 degrees. In one embodiment, the internal tubular surface 60 may have a diameter of approximately 8 mm and an axial length of approximately 3 mm.

FIG. 5 is a longitudinal cross-sectional view of the piston 28. The piston 28 may have a conical tip 62, an o-ring 34, a tubular surface 64, a plateau shaped indentation 66, and a locking element 68. The plateau shaped indentation 66 may provide a seating surface or gland for the o-ring 34. The piston 28 may have other configurations including those with fewer or additional components. In one embodiment, the piston 28 may have a longitudinal length of approximately 22 mm.

The conical tip 62 may have a substantially smooth conical exterior surface. The conical tip 62 may be in transition with the plateau shaped indentation 66 after the conical tip 62 curves to become substantially parallel to the longitudinal axis of the piston 28. The curved portion of the conical tip 62 is convex in shape. In one embodiment, the curved portion of the conical tip 62 corresponds to a concave surface (not shown) of the chamber 18 (FIG. 1). In another embodiment, the axial length of the conical tip 62 may be approximately 4 mm.

The plateau shaped indentation 66 may have a distal surface 70, a cylindrical surface 72, and a proximal surface 74. The distal and proximal surfaces 70, 74 of the piston 28 may both include a flat surface approximately orthogonal to the longitudinal axis of the piston 28. Both the distal and proximal surfaces 70, 74 may be annular in shape. In one embodiment, the distal surface 70 of the piston 28 may have an outer diameter of approximately 12 mm. In another embodiment, the distance from the distal surface 70 to the proximal surface 74 may be approximately 2 mm.

The cylindrical surface 72 may be substantially parallel to the longitudinal axis of the piston 28. The cylindrical surface 72 may intersect both the distal and proximal surfaces 70, 72 at an angle of approximately 90 degrees. The distal surface 70, the cylindrical surface 72, and the proximal surface 74 may form a generally u-shaped indentation or recess into the exterior of the piston 28. In one embodiment, the cylindrical surface 72 may have a diameter of approximately 10 mm.

The tubular surface 64 may be smooth and approximately parallel to the longitudinal axis of the piston 28. The tubular surface 64 may intersect the proximal surface 74 at an angle of approximately 90 degrees. In one embodiment, the tubular surface 64 may have an axial length of approximately 3 mm and an outer diameter of approximately 12 mm.

The o-ring 34 may be sized to fit the cylindrical surface 72 of the plateau shaped indentation 66. The distal surface 70 and the proximal surface 74 may prevent significant axial movement of the o-ring 34. The cylindrical surface 72 may have a number of grooves (not shown) or longitudinal indentations extending the axial length of the cylindrical surface 72. The grooves may be of the type disclosed in non-provisional application Ser. No. 09/875,532, filed on Jun. 6, 2001, entitled "High Pressure Injection Syringe." In use, the grooves may provide for air aspiration under the o-ring 34 as the piston 28 is advanced into the interior of the chamber 18 (FIG. 1).

The locking element 68 may have a parallel surface 76, an annular rim 78, a tapered surface 80, and an annular surface 82. The locking element 68 may have a cross-sectional area orthogonal to the longitudinal axis of the piston 28 that decreases from the annular rim 78 to the annular surface 82. In one embodiment, the locking element 68 may have an outer diameter of approximately 7 mm at the annular rim 78 and an outer diameter of approximately 6 mm at the annular surface 82.

The parallel surface 76 may be smooth and cylindrical in shape. The parallel surface 76 may be substantially parallel to the longitudinal axis of the piston 28. In one embodiment, the parallel surface 76 may have an axial length of approximately 3 mm.

The annular rim 78 may be smooth and generally flat. The annular rim 78 may be substantially orthogonal to the longitudinal axis of the piston 28. The annular rim 78 may intersect the parallel surface 76 at an angle of approximately 90 degrees.

The tapered surface 80 may be smooth and conical in shape. The tapered surface 80 may intersect the annular rim 78 at an angle less than 90 degrees. In one embodiment, the tapered surface 80 may have an axial length of approximately 3 mm.

The annular surface 82 may be smooth and generally flat. The annular surface 82 may be substantially orthogonal to the longitudinal axis of the piston 28. The annular surface 82 may intersect the tapered surface 80 at an angle greater than 90 degrees.

The piston 28 may have at least one internal groove 84 that may provide a hollow indentation into the body of the piston 28. The internal groove 84 may provide flexibility for insertion into the internal locking mechanism 52 (FIG. 4). The internal groove 84 may allow the exterior of the piston 28 to compress as the piston 28 is inserted into the internal locking mechanism 52.

The piston 28 may be coupled to the threaded rod 14 (FIG. 4) by inserting the piston 28 into the internal locking mechanism 52 (FIG. 4), such that the piston 28 snaps into place. As the piston 28 is inserted into the internal locking mechanism 52, the tapered surface 80 may engage the internal tapered surface 56 (FIG. 4). Eventually, the annular rim 78 of the piston 28 slides over the internal annular surface 58 (FIG. 4) and the locking element 68 snaps into the internal locking mechanism 52. After the piston 28 is coupled to the threaded rod 14, any force that would tend to inadvertently separate the piston 28 from the threaded rod 14 will cause the internal annular surface 58 to mate with annular rim 78, which may prevent the piston 28 and threaded rod 14 from uncoupling.

In another embodiment, the piston 28 may be insert-molded into the threaded rod 14 (FIG. 4). Insert-molding the piston 28 into the threaded rod 14 may enhance the strength of the high pressure dispenser 10.

FIG. 6 is a longitudinal view of the chamber 18. The chamber 18 may have a conduit 102, a nozzle 104, a locking mechanism 106, and at least one tab 108. Medicinal mixtures may be dispensed from the conduit 102 via the nozzle 104. The chamber 18 may have other configurations including those with fewer or additional components. In one embodiment, the chamber 18 may have a longitudinal length of approximately 106 mm. In another embodiment, the chamber 18 is a syringe barrel. However, alternate chambers also may be used.

The nozzle 104 may be tubular in shape and have a hollow cylindrical cavity 105. In one embodiment, the nozzle 104 may have a cylindrical cavity 105 approximately 11 mm in length.

The conduit 102 may have a smooth interior cylindrical surface 110 on the interior of the chamber 18. In one embodiment, the smooth-interior cylindrical surface 110 may have a diameter orthogonal to the longitudinal axis of the chamber 18 of approximately 13 mm.

The conduit 102 may be in fluid communication with the nozzle 104. The chamber 18 may have a concave surface 111 in between the smooth interior cylindrical surface 110 of the conduit 102 and the cylindrical cavity 105 of the nozzle 104. The concave surface 111 may be smooth and curved inwardly toward the center of the conduit 102. The convex portion of the conical surface 62 (FIG. 5) of the piston 28 (FIG. 5) may be configured to uniformly mate with the concave surface 111 of the chamber 18. The concave surface 111 may transition through a convex surface 113 to the nozzle 104. The concave surface 111 and the convex surface 113 may smooth the flow of the medical mixture from the conduit 102 through the nozzle 104.

The chamber 18 may have a smooth cylindrical exterior 112. In one embodiment, the smooth cylindrical exterior 112 may have a diameter orthogonal to the longitudinal axis of the chamber 18 of approximately 19 mm.

The locking mechanism 106 may be utilized to interconnect the chamber 18 and the handle 16 (FIG. 1). The locking mechanism 106 may have an orthogonal surface 114, an oval surface 116, and a curved surface 118. The orthogonal surface 114 may be smooth, generally flat, and have an oval cross-section. The orthogonal surface 114 may be approximately orthogonal to the longitudinal axis of the chamber 18. The oval surface 116 may be smooth and oval in shape along the longitudinal axis of the chamber 18. In one embodiment, the oval surface 116 may have an axial length of approximately 8 mm.

The curved surface 118 may be rounded inward toward the center of the locking mechanism 106 and connect the oval surface 116 with the smooth cylindrical exterior 112 of the chamber 18. The juxtaposition of the orthogonal surface 114, the oval surface 116, and the curved surface 118 may effectuate a generally u-shaped exterior cross-section for the locking mechanism 106.

The chamber 18 also may have at least one tab 108 located on the smooth cylindrical exterior 112 in proximity to the curved surface 118. Each tab 108 may facilitate positive snap-in engagement with a corresponding notch or recess (not shown) on the handle 16. In one embodiment, the axial length of the tabs 108 may be approximately 5 mm. In another embodiment, the chamber 18 may have at least one notch located on the smooth cylindrical exterior 112 in proximity to the curved surface 118. Each notch may be a curved indentation or recess into the smooth cylindrical exterior 112. Each notch on the chamber 18 may facilitate positive snap-in engagement with a corresponding tab on the handle 16.

FIG. 7 is a front elevation view of the chamber 18. The chamber 18 may have a nozzle 104, a locking mechanism 106, and at least one tab 108. The locking mechanism may have an oval exterior surface 116. The chamber 18 may have other configurations including those with fewer or additional components. In one embodiment, each tab 108 may be a curved protuberance from the smooth cylindrical exterior 112 of the chamber 18.

FIG. 8 is a longitudinal cross-sectional view of the threaded insert 120. The threaded insert 120 may have internal threads 122, a first cylindrical surface 124, and a second cylindrical surface 126. The threaded inset 120 may have other configurations including those with fewer or additional components.

The internal threads 122 may extend the entire longitudinal length of the threaded insert 120. The internal threads 122 may engage the threads of the threaded plunger 14 (FIG. 1) in use.

The first cylindrical surface 124 may be smooth and constant in diameter. In one embodiment, the first cylindrical surface 124 may have a diameter of approximately 14 mm and may have an axial length of approximately 6 mm.

The second cylindrical surface 126 may have a curved indentation 128, and, similar to the threaded rod 14, may have at least one knurl or indentation parallel to the axial length of the threaded insert 120. The knurl may help prevent rotation of the threaded insert 120 as the plunger 26 (FIG. 2) is turned by a user.

The curved indentation 128 may form a semi-circular indentation into the exterior of the threaded insert 120. In one embodiment, the second cylindrical surface 126 may have an axial length of approximately 6 mm and have a diameter at the crest of the semi-circular indentation of the curved indentation 128 of approximately 18 mm.

The annular insert surface 130 may provide a transition from the first cylindrical surface 124 to the second cylindrical surface 126 as the diameter of the threaded insert 120 expands from that of the first cylindrical surface 124 to that of the second cylindrical surface 126. The annular insert surface 130 may be smooth and generally flat.

FIG. 9 is a cross-sectional view of the handle 16 of the present invention along line 9-9 of FIG. 1. The handle 16 may have two overmolded handle sides (not shown), two plastic handle sides 142, interior ribs 134, and a threaded insert 120. The unique features of the handle 16 may enhance the capability of the user to operate and control the high pressure dispenser 10, as well as the ergonomic characteristics of the dispenser 10. The handle 16 may have other configurations including those with fewer or additional components.

The threaded insert 120 may be insert-molded into the handle 16. The threaded insert 120 may be fabricated from either plastic or metal, such as stainless steel. By insert-molding the threaded insert 120 into the handle 16, the strength of the handle 16 may be increased.

The interior ribs 134 may have a flat upper surface 136 and a flat lower surface 138. The flat upper and lower surfaces 136, 138 are substantially parallel to the longitudinal axis of the threaded rod 14 (FIG. 1) in use. In one embodiment, the width of each interior rib 134 from the flat upper surface 136 to the flat lower surface 138 may be approximately 3 mm. The rib spacing 140 may be the distance between one flat lower surface 138 to the next flat lower surface 138. In another embodiment, the rib spacing 140 may be approximately 9 mm.

The interior ribs 134 may be coupled by two plastic handle sides 142. The interior ribs 134 and the plastic handle sides 142 may be made of hard plastic. In one embodiment, the maximum horizontal exterior distance 144 between opposite plastic handle sides 142 may be approximately 38 mm and the maximum horizontal interior distance 146 between opposite plastic handle sides 142 may be approximately 28 mm.

In between each pair of corresponding interior ribs 134 is a gap 132. During the manufacturing process, each gap 132 is filled with overmolded soft rubber material. The overmolded soft rubber fills the gaps 132 to the extent that the overmolded soft rubber forms the majority of the two exterior longitudinal sides of the handle 16 in between the two plastic handle sides 142.

The interior ribs 134 may have teeth 148. The teeth 148 may form a three sided indentation into the interior ribs 134. The teeth 148 may be in vertical alignment within the interior of the handle 16. The teeth 148 of the interior ribs 134 form a channel for the overmolded soft rubber material to flow through during the overmolding process.

The handle 16 may have a top exterior ridge 152. The top exterior ridge 152 may be primarily flat and smooth. The handle 16 also may have a bottom exterior ridge 156. The bottom exterior ridge 156 may be primarily flat and smooth. In one embodiment, the distance from the top exterior ridge 152 to the bottom exterior ridge 156 may be approximately 20 mm.

The handle also may have an insert surface 162. The insert surface 162 may be flat and smooth. The insert surface 162 may be flush with the threaded insert 20. In one embodiment, the horizontal width of the insert surface 162 may be approximately 33 mm.

FIG. 10 is a perspective view of the handle 16 of the present invention. The handle 16 may have two plastic handle sides 142, a number of interior ribs 134, and a threaded insert 120. The handle 16 may have other configuration's including those with fewer or additional components.

The bottom exterior ridge 156 may have a notch 160. The notch 160 may be a curved indentation or recess into the exterior of the bottom exterior ridge 156. The top exterior ridge 152 (FIG. 9) also may have a notch (not shown). In another embodiment, either the bottom exterior ridge 156 or the top exterior ridge 152 may have a tab (not shown), or both. Each tab may protrude outward from either the bottom or the top exterior ridge 156, 152.

In one embodiment, the tab or tabs 108 of the chamber 18 may be sized to fit into the corresponding notch or notches 160 of the handle 16. Alternatively, the chamber 18 may have one or more notches and the handle 16 may have one or more tabs. The tab or tabs of the handle 16 may be sized to fit the corresponding notch or notches of the chamber 18 and facilitate positive snap-in engagement.

FIG. 11 is a cross-sectional view of the interior of the handle 16 along lines 11-11 of FIG. 9. The handle 16 may have at least one interior rib 134 with teeth 148, two plastic handle sides 142, and two overmolded handle sides 141. The handle 16 may have other configurations including those with fewer or additional components.

The plastic handle sides 142 may be made of hard plastic. The overmolded handle sides 141 may be made primarily of soft overmolded rubber material 143. During the overmolding process, soft overmolded rubber material 143 fills the gaps 132 (FIG. 9) in between each pair of corresponding interior ribs 134. Each handle side 141, 142 may be generally smooth and may have a primarily flat portion. The primarily flat portion of each handle side 141, 142 may be in curved communication with the adjacent handle side 142, 141.

FIG. 12 is a cross-sectional view of the handle 16 along line 12-12 of FIG. 9. The handle 16 may have a threaded insert 120. The handle 16 may have other configurations including those with fewer or additional components.

The handle 16 may have a back handle surface 174. The back handle surface 174 may be flat and flush with the threaded insert 120. In one embodiment, the width of the handle 16 from the insert surface 162 to the back handle surface 174 may be approximately 13 mm.

The handle 16 also may have a front handle surface 176. The front handle surface 176 may be flat and smooth. In one embodiment, the width of the handle 16 from the front handle surface 176 to the back handle surface 174 may be approximately 30 mm.

The handle 16 may have a handle top 178 and a handle bottom 180. Both the handle top and bottom 178, 180 may be smooth. In one embodiment, the length of the handle 16 from the handle top 178 to the handle bottom 180 may be approximately 136 mm.

The chamber 18 (FIG. 6) may be coupled to the handle 16. By sliding the narrow embodiment of the oval locking mechanism 106 (FIG. 6) into the handle 16, such that the orthogonal surface 114 (FIG. 6) is flush with the insert surface 162, and rotating the chamber 18 in a counter-clockwise direction, the locking mechanism 106 snuggly couples the chamber 18 to the handle 16. Additionally, the tab or tabs 108 (FIG. 6) of the chamber 18 may be sized to fit the corresponding notch or notches 160 of the handle 16, which may help couple the chamber 18 to the handle 16.

FIG. 13 is a longitudinal view of the handle 16 which may have four exterior sides. Two plastic handle sides 142 may be made of hard plastic. One or both overmolded handle sides 141 may have an exterior frame made of hard plastic and an interior surface made of overmolded soft rubber. Additionally, the majority of each overmolded handle side 141 may be made of overmolded soft rubber material. The handle 16 may have other configurations including those with fewer or additional components.

While the preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

It is therefore intended that the foregoing detailed description be regarded as illustrative rather than limiting, and that it be understood that it is the following claims, including all equivalents, that are intended to define the spirit and scope of this invention.

What is claimed is:

1. A high pressure dispenser for the application of a medicinal mixture to a desired location, the dispenser comprising:
   a handle;
   a chamber that receives a medicinal mixture coupled to the handle;
   a threaded region within and fixed with respect to the handle;
   a threaded rod in threaded engagement with the threaded region; and
   a knob coupled to the threaded rod;
   the dispenser characterized in that:
   the dispenser includes at least one insert-molded component, wherein the at least one insert-molded component includes at least one of a threaded insert providing the threaded region insert-molded into the handle and a threaded rod insert-molded into the knob.

2. The dispenser of claim 1, characterized in that the threaded insert includes metal or plastic.

3. The dispenser of claim 1, characterized in that the handle includes hard plastic and overmolded soft rubber.

4. The dispenser of claim 1, characterized in that the threaded rod includes metal.

5. The dispenser of claim 1, characterized in that an exterior surface of the chamber comprises at least one tab dimensioned to engage with at least one corresponding notch on an exterior surface of the handle.

6. The dispenser of claim 1, characterized in that an exterior surface of the chamber comprises at least one notch dimensioned to engage with at least one corresponding tab on an exterior surface of the handle, wherein the notch is a curved indentation into a cylindrical exterior of the chamber.

7. The dispenser of claim 1, characterized in that the handle comprises four exterior longitudinal sides.

8. The dispenser of claim 1, characterized in that the knob has an axial length approximately equal to or greater than the diameter of the knob.

9. The dispenser of claim 1, characterized in that the knob has at least one symmetrical rib and a plurality of longitudinal ribs, with at least one longitudinal rectangular cavity between a pair of the longitudinal ribs.

10. The dispenser of claim 1, characterized in that the chamber comprises an interior cylindrical surface and a nozzle in fluid communication, and the interior of the chamber has a concave surface in between the interior cylindrical surface and the nozzle.

11. The dispenser of claim 1, characterized in that the threaded rod is coupled to a piston, the piston is insert molded into the threaded rod.

12. The dispenser of claim 1, characterized in that the threaded rod includes an internal locking mechanism, and further including a piston having at least a portion snapped into said internal locking mechanism.

13. The dispenser of claim 1, characterized in that said chamber includes an external locking mechanism having an orthogonal surface and a tab distal of said orthogonal surface.

14. The dispenser of claim 1, characterized in that the at least one insert-molded component includes a threaded insert providing the threaded region insert-molded into the handle, and wherein said threaded insert includes internal threads and an external surface, the external surface having a curved indentation.

15. The dispenser of claim 14, characterized in that the threaded insert includes at least one knurl or indentation parallel to the axial length of the threaded insert.

16. A high pressure medicinal dispenser, comprising:
    a handle having a grip section for accommodating a user's hand and an insert section having a threaded region, a slot adjacent and fixed with respect to the threaded region, and top and bottom exterior ridges;
    a chamber for holding a medicinal mixture, the chamber having an upper portion interconnected to the handle in the slot and between the top and bottom exterior ridges, and an interior that communicates with the threaded region of the handle;
    a threaded rod laterally offset from the grip section and extending through the insert section and threadedly engaging the threaded region of the handle, the rod being substantially collinear with the chamber, wherein the threaded rod is rotatable within the threaded region while the handle with the chamber is held; and
    a knob fixed to the threaded rod for turning the rod with respect to the handle and chamber.

17. The dispenser of claim 16, wherein the threaded region is an internally-threaded insert that is insert-molded into the handle.

18. The dispenser of claim 16, wherein the rod is insert-molded into the knob.

19. The dispenser of claim 16, wherein the chamber is insertable and removable from the handle by moving the chamber upper portion with respect to the slot laterally with respect to the longitudinal axis of the chamber and to the longitudinal axis of the handle.

* * * * *

UNITED STATES PATENT AND TRADEMARK OFFICE
CERTIFICATE OF CORRECTION

| | | |
|---|---|---|
| PATENT NO. | : 8,372,030 B2 | Page 1 of 1 |
| APPLICATION NO. | : 10/593949 | |
| DATED | : February 12, 2013 | |
| INVENTOR(S) | : Christopher G. Dixon | |

It is certified that error appears in the above-identified patent and that said Letters Patent is hereby corrected as shown below:

Title Page item (86), replace "PCT/US2005/100036" with --PCT/US2005/010036--.

Signed and Sealed this
Twentieth Day of August, 2013

Teresa Stanek Rea
*Acting Director of the United States Patent and Trademark Office*